United States Patent [19]

Murahashi et al.

[11] Patent Number: 4,596,874
[45] Date of Patent: Jun. 24, 1986

[54] SYNTHESIS OF NITRONE FROM SECONDARY AMINE

[75] Inventors: Shun-Ichi Murahashi, Ikeda; Hitoshi Mitsui, Suita, both of Japan

[73] Assignee: The President of Osaka University, Osaka, Japan

[21] Appl. No.: 587,383

[22] Filed: Mar. 8, 1984

[30] Foreign Application Priority Data

Mar. 9, 1983 [JP] Japan .................................. 58-38436

[51] Int. Cl.⁴ .................. C07D 498/04; C07D 211/94; C07D 207/46; C07D 215/60; C07D 217/10
[52] U.S. Cl. ..................................... 546/141; 544/73; 544/63; 546/153; 546/290; 546/347; 548/542; 564/271; 564/278; 564/248; 564/272; 564/275
[58] Field of Search ............... 564/271, 272, 278, 275, 564/248; 546/141, 142, 255, 347, 153, 290; 548/542

[56] References Cited

U.S. PATENT DOCUMENTS 3,467,711  9/1969  Bader et al. ........................ 564/300
3,494,924  2/1970  Bonetti et al. ..................... 548/542

FOREIGN PATENT DOCUMENTS 971307  1/1959  Fed. Rep. of Germany ...... 564/248

OTHER PUBLICATIONS

Murahashi et al., Rx of N and N,N Subst. by Dioxylamines with Pd Catalyst. Pergamon Press/Tetrahed. Letters, vol. 24, No. 10, 1049–1052.

Ginsberg, *Concerning Amines*, Pergamon Press, 1967, pp. 87–88.

Allinger et al., *Organic Chemistry*, Worth Publishers 1971, pp. 575–576.

House, Modern Synthetic Reactions, 2nd Edition, Benjamin/Cummings Co., CA (1972), pp. 330–335.

Primary Examiner—Glennon H. Hollrah
Assistant Examiner—Dara L. Dinner
Attorney, Agent, or Firm—Robert E. Burns; Emmanuel J. Lobato; Bruce L. Adams

[57] ABSTRACT

A nitrone is synthesized from a secondary amine by reacting a compound represented by the following general formula

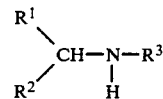

wherein $R^1$ and $R^2$ mean individually a hydrogen atom or an alkyl or aryl group and $R^3$ denotes an alkyl or aryl group with a peroxide in the presence of a catalyst selected from the group consisting of tungsten compounds, molybdenum compounds, vanadium compounds, titanium compounds, palladium compounds, rhodium compounds, ruthenium compounds and nickel compounds. This process provides the nitrone by one-step oxidation of the secondary amine.

9 Claims, No Drawings

SYNTHESIS OF NITRONE FROM SECONDARY AMINE

BACKGROUND OF THE INVENTION

1. Field of the Invention

This invention relates to a process for synthesizing a nitrone from a secondary amine.

2. Description of the Prior Art

No process has heretofore been developed to synthesize a nitrone in a single step by the oxidation of a secondary amine.

It has been well known that the oxidation of a secondary amine in the presence of a metal catalyst provides an N,N-disubstituted hydroxyamine which is a precursor of a nitrone. However, such a conventional process is accompanied by problems in that the yield of the intended product is low and many by-products are formed.

SUMMARY OF THE INVENTION

With the foregoing in view, an object of this invention is to provide a process capable of obtaining, in a single step and with good efficiency, a nitrone which is a useful intermediate in the field of organic syntheses, from a secondary amine in the presence of a metal compound catalyst.

In one aspect of this invention, there is thus provided a process for synthesizing a nitrone from a secondary amine, which process comprises reacting a compound represented by the following general formula:

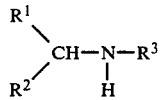

wherein $R^1$ and $R^2$ mean individually a hydrogen atom or an alkyl or aryl group and $R^3$ denotes an alkyl or aryl group with a peroxide in the presence of a catalyst selected from the group consisting of tungsten compounds, molybdenum compounds, vanadium compounds, titanium compounds, palladium compounds, rhodium compounds, ruthenium compounds and nickel compounds.

Accordingly, the process of this invention permits the synthesis of a nitrone, which is a useful compound in the field of organic syntheses, directly from a secondary amine. Furthermore, a dipolar cyclo-addition product of such a nitrone which addition product is a precursor of a physiologically-active substance such as an alkaloid or the like may be obtained in a single step provided that the oxidation of such a secondary amine is effected in the simultaneous presence of an alkene or alkenyl compound. Therefore, the process of this invention is an extremely useful reaction from the industrial viewpoint.

DESCRIPTION OF THE PREFERRED EMBODIMENT

In the above general formula, $R^1$, $R^2$ and $R^3$ may all be alkyl groups. Such alkyl groups may be saturated or unsaturated alkyl groups, cycloalkyl groups, aralkyl groups, or alkyl groups containing one or more hetero-ring residual groups or substituent groups.

$R^1$, $R^2$ and $R^3$ may also be coupled together with the carbon atoms to which they are connected, optionally via one or more hetero atoms, to form a saturated or unsaturated ring. The thus-formed saturated or unsaturated ring may contain one or more substituent groups bonded thereon. Among the preferred secondary amines are dibutylamine, diisopropylamine, dibenzylamine, benzylmethylamine, pyrrolidine, piperidine, 2-methylpiperidine, 1, 2, 3, 4-tetrahydroisoquinoline, 1-(3-benzyloxy-4-methoxy)benzyl-7-benzyloxy-6-methoxy-1,2,3,4-tetrahydroisoquinoline, and 1-(3-hydroxy-4-methoxy) benzyl-7-hydroxy-6-methoxy-1,2,3,4-tetrahydroisoquinoline.

In the process of this invention, the reaction may be carried out with or without a solvent. A polar solvent or non-polar solvent may be used. The reaction temperature may range from $-10°$ C. to $+150°$ C. It is possible to cause a a compound susceptible of undergoing an addition reaction with the nitrone to be present simultaneously in the reaction system. An addition product of the nitrone can be obtained with good efficiency particularly when an olefine or olefinic compound is allowed to exist at the same time.

Reactions are carried out under nitrogen in the below-described Examples. However, use of such an $N_2$ atmosphere is not essential.

Olefin addition products of nitrones, which can be obtained in accordance with the process of this invention, are precursors of physiologically-active substances such as alkaloids and are thus useful materials.

Addition products of nitrones can be synthesized directly when their corresponding secondary amines are subjected to oxidation in the simultaneous presence of their corresponding olefins. Accordingly, the process of this invention is expected to be very effective for industrial applications.

In the process of this invention, a nitrone is obtained by reacting a corresponding secondary amine with a peroxide in the presence of a metal compound catalyst. As the oxidant, a peroxide such as hydrogen peroxide, m-chloroperbenzoic acid or t-butyl hydroperoxide is preferred. It is possible to use, as the catalyst, palladium black, palladium chloride, vanadium pentoxide, acetylacetonatovanadium oxide, acetylacetonatomolybdenum oxide, titanium tetrabutoxide monomer, tungstic anhydride, sodium tungstate or the like. However, a hydrogen peroxide-sodium tungstate system gives the best results. As the solvent, a polar solvent such as dimethylsulfoxide or dimethylformamide may be employed. However, water, methanol, water-alcohol mixed solvents and the like also gave good results. Experiments:

Certain experimental reactions were carried out using methanol or water as a solvent and hydrogen peroxide in an amount 3 times in chemical equivalent the respective secooondary amines in the presence of sodium tungstate as a catalyst. Results are shown in Table 1.

TABLE 1

| Secondary amine | Solvent | Reaction product | Isolated yield (%) |
|---|---|---|---|
| $(C_4H_9)_2NH$ | $CH_3OH$ | $C_4H_9N^+(O^-)=CHC_3H_7$ | 89 |
| $(i-C_3H_7)_2NH$ | $CH_3OH$ | $i-C_3H_7N^+(O^-)=C(CH_3)_2$ | 74 |
| $(C_6H_5CH_2)_2NH$ | $CH_3OH$ | $C_6H_5CH_2N^+(O^-)=CHC_6H_5$ | 85 |
| $C_6H_5CH_2NHCH_3$ | $CH_3OH$ | $C_6H_5CH=N^+(O^-)-CH_3$ | 34 |

TABLE 1-continued

| Secondary amine | Solvent | Reaction product | Isolated yield (%) |
| --- | --- | --- | --- |
| | | C₆H₅CH=N—OH | 33 |
|  | H₂O |  | 37 |
|  | H₂O |  | 40 |
|  | H₂O |  | 71 |
|  | CH₃OH |  | 89 |
|  | CH₃OH |  | 60 |
|  | CH₃OH |  | 32 |

The experimental reactions were conducted under the following conditions:
Secondary amine: 5 mmol
Sodium tungstate: 0.2 mmol
Hydrogen peroxide: 15 mmol
Solvent methanol: 10 ml or water: 2 ml
Reaction temperature: 0° C.
Reaction time: 3 hrs.

General procedure was the same as that followed in the following Example 1:

EXAMPLE 1

Synthesis of 2-methyl-3,4,5,6-tetrahydropyridinoisoxazole

A magnetic stirrer was placed in an eggplant-type flask having an internal volume of 20 ml, followed by an addition of sodium tungstate (66 mg, 0.2 mmol). The internal atmosphere was substituted with nitrogen. Thereafter, water (2 ml) and 2-methylpiperidine (495 mg, 5.0 mmol) were added successively, followed by an addition with stirring of a 30% solution of hyrogen peroxide in water (1.7 g, 15.0 mmol) at 0° C, with ice-cooling over 10 minutes. After completion of the dropwise addition, the resultant mixture was stirred at room temperature for 6 hours. The reaction mixture was extracted twice with methylene chloride (50 ml). The organic layer was washed with saturated saline (20 ml) and then dried with magnesium sulfate. After driving off the solvent, the residue was isolated and purified by silica gel chromatography to obtain 2-methyl-3,4,5,6-tetrahydropyridine-1-oxide (429 mg, 76%).

EXAMPLE 2

Synthesis of 3,4-dihydroisoquinoline-2-oxide

A magnetic stirrer was placed in a 300-ml eggplant-type flask, followed by an addition of sodium tungstate (0.33 g, 1.0 mmol). The internal atmosphere was replaced with nitrogen. Thereafter, methanol (200 ml) and 1,2,3,4-tetrahydroisoquinoline (6.65 g, 50.0 mmol) were added successively. To the resulting mixed solution, a 30% solution of hydrogen peroxide in water (17.0 g, 150.0 mmol) was added dropwise with stirring at 0° C. in the course of 30 minutes. After stirring the mixture at room temperature for 3 hours, the solvent was driven off under reduced pressures. The residue was taken up in methylene chloride (100 ml) and then washed twice with saturated saline (30 ml). The organic phase was separated and then dried with anhydrous magnesium sulfate. The solvent was driven off under reduced pressures, thereby obtaining an yellowish oily product. The oily product was subjected to silica gel column chromatography. The column as eluted with acetone to obtain 3,4-dihydroisoquinoline-2-oxide as a nitrone (6.54 g, 89%).

EXAMPLE 3

2-Butoxy-1,2,4,5,6-10b-hexahydroisoquinolinoisoxazole (General procedure for the oxidation of a secondary amine in the presence of an alkene)

A magnetic stirrer was placed in a 20-ml flask with a side arm on which a condenser is fitted. Then, sodium tungstate (66 mg, 0.2 mmol) was added and the internal atmosphere was substituted with nitrogen.

Thereafter, water (3 ml), butyl vinyl ether (1.0 g, 10.0 mmol) and tetrahydroisoquinoline (665 mg, 5.0 mmol) were added successively. The resultant mixture was heated to 90° C. Then, a 30% solution of hydrogen peroxide in water (1.2 g, 10.6 mmol) was added dropwise over 30 minutes. The resulting mixture was stirred for 1 hour at the same temperature and the reaction mixture was cooled down to room temperature, followed by an addition of chloroform (100 ml). The organic layer was washed with saturated saline (10 ml) and dried with anhydrous magnesium sulfate. After driving off the solvent, a yellowish oily product was obtained. The oily product was subjected to thin-layer chromatography (silica gel, hexane/ethyl acetate=3/1) to obtain 2-butoxy-1,2,4,5,6,10b-hexahydroisoquinolinoisoxazole (950 mg, 77%).

EXAMPLES 4–7

Some addition products of nitrones were also prepared under the same reaction conditions as in Example 3. Results are given in Table 2, together with the results obtained in Example 3.

TABLE 2

| Secondary amine | Alkene or Alkenic compound | Reaction product | Isolated yield (%) |
|---|---|---|---|
| piperidine (NH) | CH₂=CH-OBu | piperidine N-O-CH₂CH₂-OBu | 54 |
| piperidine (NH) | CH₂=CH-ph | piperidine N-O-CH₂CH₂-ph | 15 |
| piperidine (NH) | CH₂=CH-CH₂-OTHP | piperidine N-O-CH₂CH(OTHP)- | 24 |
| morpholine (NH) | CH₂=CH-OBu | morpholine N-O-CH₂CH₂-OBu | 30 |
| 1,2,3,4-tetrahydroisoquinoline (NH) | CH₂=CH-OBu | hexahydroisoquinolinoisoxazole-OBu | 77 |

EXAMPLE 8

The oxidation of dibutylamine was carried out using various oxidants and metal compound catalysts given in Table 3. Results are summarized also in Table 3.

TABLE 3

| Entry | Catalyst | Oxidant | Molar Ratio | Solvent | Conv. (%) | Yield (%) |
|---|---|---|---|---|---|---|
| 1 | Pd—black | $H_2O_2$ | 1.0 | $CH_3OH$ | 0 | — |
| 2 | $V_2O_5$ | $H_2O_2$ | 3.0 | $CH_3OH$ | 20 | 50 |
| 3 | $VO(acac)_2$ | $H_2O_2$ | 3.0 | $CH_3OH$ | 10 | 95 |
| 4 | $MoO_2(acac)_2$ | $H_2O_2$ | 3.0 | $CH_3OH$ | 30 | 95 |
| 5 | $Ti(OC_4H_9)_4$ | $H_2O_2$ | 3.0 | $CH_3OH$ | 30 | 96 |
| 6 | $WO_3$ | $H_2O_2$ | 3.0 | $CH_3OH$ | 10 | 90 |
| 7 | $H_2WO_4$ | $H_2O_2$ | 3.0 | $CH_3OH$ | 25 | 95 |
| 8 | $Na_2WO_4.2H_2O$ | $H_2O_2$ | 1.0 | $CH_3OH$ | 35 | 98 |
| 9 | $Na_2WO_4.2H_2O$ | $H_2O_2$ | 2.0 | $CH_3OH$ | 45 | 98 |
| 10 | $Na_2WO_4.2H_2O$ | $H_2O_2$ | 3.0 | $CH_3OH$ | 100 | 98(89) |
| 11 | $Na_2WO_4.2H_2O$ | $H_2O_2$ | 3.0 | $H_2O$ | 80 | 98(60) |
| 12 | $Na_2WO_4.2H_2O$ | $t-C_4H_9OOH$ | 3.0 | $C_6H_6$ | 0 | — |

What is claimed is:

1. A process for synthesizing a nitrone from a secondary amine, which process comprises reacting a secondary amine represented by the formula:

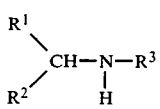

wherein
$R^1$ and $R^2$ individually represent a hydrogen atom or saturated, unsaturated or cyclo-alkyl, phenyl, or benzyl group,
$R^3$ denotes a saturated, unsaturated or cyclo-alkyl, phenyl or benzyl group, and
two or three of said $R^1$, $R^2$ and $R^3$ together may be optionally coupled optionally via one or more heteroatoms selected from the group of O, N and S to form a cyclic group of 5 to 7 members which may be additionally benzo-fused and which may optionally contain substituent groups
with hydrogen peroxide in the presence of a catalyst selected from the group consisting of a tungsten compound, molybdenum compound, vanadium compound and titanium compound, whereby a nitrone corresponding to said secondary amine is obtained in a single step.

2. The process as claimed in claim 1, wherein the catalyst is vanadium pentoxide, acetylacetonatovanadium oxide, acetylacetonatomolybdenum oxide, titanium tetrabutoxide monomer, tungstic anhydride or sodium tungstate.

3. The process as claimed in claim 1, wherein the reaction is carried out at a temperature in the range of $-10°$ C.$-+150°$ C.

4. The process as claimed in claim 1, wherein the reaction is carried out in an $N_2$ atmosphere.

5. The process as claimed in claim 1, wherein the reaction is carried out in a polar solvent.

6. The process as claimed in claim 5, wherein the solvent is water, methanol, or a water-alcohol solvent.

7. The process as claimed in claim 1, wherein the secondary amine is selected from the group consisting of dibutylamine, diisopropylamine, dibenzylamine, benzylmethylamine, pyrrolidine, piperidine, 2-methylpiperidine, 1,2,3,4-tetrahydroisoquinoline, 1-(3-benzyloxy-4-methoxy)benzyl-7-benzyloxy-6-methoxy-1,2,3,4-tetrahydroisoquinoline; or 1-(3-hydroxy-4-methoxy)benzyl-7-hydroxy-6-methoxy-1,2,3,4-tetrahydroisoquinoline.

8. The process as claimed in claim 1 in which said secondary amine is reacted with about 3 moles of said peroxide per mole of said secondary amine.

9. The process as claimed in claim 1 in which the catalyst is sodium tungstate.

* * * * *